(12) United States Patent
Studer et al.

(10) Patent No.: US 7,377,921 B2
(45) Date of Patent: May 27, 2008

(54) DAMPING ELEMENT AND DEVICE FOR STABILIZATION OF ADJACENT VERTEBRAL BODIES

(75) Inventors: Armin Studer, Winterthur (CH); Robert Frigg, Bettlach (CH)

(73) Assignee: Synthes (U.S.A.), West Chester, PA (US)

( * ) Notice: Subject to any disclaimer, the term of this patent is extended or adjusted under 35 U.S.C. 154(b) by 508 days.

(21) Appl. No.: 10/497,794

(22) PCT Filed: Mar. 28, 2002

(86) PCT No.: PCT/CH02/00180

§ 371 (c)(1),
(2), (4) Date: Nov. 4, 2004

(87) PCT Pub. No.: WO03/047442

PCT Pub. Date: Jun. 12, 2003

(65) Prior Publication Data

US 2005/0056979 A1  Mar. 17, 2005

(30) Foreign Application Priority Data

Dec. 7, 2001 (WO) .................... PCT/CH01/00705

(51) Int. Cl.
   A61B 17/56  (2006.01)
   A61F 2/30   (2006.01)
(52) U.S. Cl. ...................................... 606/61
(58) Field of Classification Search ........... 606/60, 606/61; 267/80, 81, 83, 84, 86, 91, 93
   See application file for complete search history.

(56) References Cited

U.S. PATENT DOCUMENTS 3,862,751 A * 1/1975 Schwaller ............... 267/91
3,977,397 A * 8/1976 Kalnberz et al. ............. 606/57
5,375,823 A   12/1994 Navas
5,480,401 A   1/1996 Navas (Continued)

FOREIGN PATENT DOCUMENTS

CN    88 2 01056 U    8/1988

(Continued)

OTHER PUBLICATIONS

WO 99/40866, Interspinous Stabiliser to be Fixed to Spinous Processes of Two Vertebrae, Publication Date: Aug. 19, 1999.

*Primary Examiner*—Anuradha Ramana
(74) *Attorney, Agent, or Firm*—Stroock & Stroock & Lavan LLP (57) ABSTRACT

A damping element (1) includes: (a) two spring elements (2, 4) which are coaxial with or parallel to a longitudinal axis (3) and two axially end-side connectors (5, 6), where (b) the first spring element (2) exhibits a spring rate F, (c) the second spring element (4) exhibits a spring rate f, and (d) the spring rates F and f are different. A device stabilizing adjacent vertebras, comprising (a) N pedicle screws of hooks (12), where $N \geq 3$ and where (b) each pedicle screw or pedicle hook (12) includes a receiving device (13) receiving a longitudinal affixation device (7) and where (c) an element (14) acting as a spring is inserted between two adjacent pedicle screws (12) or pedicle hooks.

14 Claims, 6 Drawing Sheets

U.S. PATENT DOCUMENTS

| | | |
|---|---|---|
| 5,540,688 A | 7/1996 | Navas |
| 5,672,175 A * | 9/1997 | Martin .................. 606/61 |
| 5,733,284 A * | 3/1998 | Martin .................. 606/61 |
| 6,267,764 B1 | 7/2001 | Elberg |
| 6,402,750 B1 * | 6/2002 | Atkinson et al. ............ 606/61 |

FOREIGN PATENT DOCUMENTS

| | | |
|---|---|---|
| DE | 1 127 671 | 4/1962 |
| DE | 1 147 494 | 4/1963 |
| EP | 0 669 109 A1 | 8/1995 |
| FR | 2 718 946 | 10/1995 |
| FR | 2 799 949 | 4/2001 |

\* cited by examiner

DAMPING ELEMENT AND DEVICE FOR STABILIZATION OF ADJACENT VERTEBRAL BODIES

CROSS-REFERENCE TO RELATED APPLICATIONS

This application claims the benefit of International Application No. PCT/CH02/00180, filed Mar. 28, 2002, which claims the benefit of International Application No. PCT/CH01/00705, filed Dec. 7, 2001. Priority is claimed to the applications listed above, which are incorporated herein by reference.

BACKGROUND OF THE INVENTION

The present invention relates to a damping element as defined in the preamble of claim 1, furthermore to a device stabilizing adjacent vertebras as defined in the preamble of claim 27.

The French patent document 2,799,949 A discloses a spinal fixing device consisting of a number of tulip-like pedicle screws which in lieu of the conventional rigid longitudinal support are connected to each other by spiral spring elements. While the length of the spiral springs is adjustable, this design only allows a change in the spring force between two adjacent pedicle screws and hence between two adjacent vertebrae. This document allows no conclusion whether the spring elements are mounted prestressed between the pedicle screws.

Another spinal fixation device is known from the European patent document 0,516,567 A, said device consisting of a number of tulip-like pedicle screws which are connected to each other by single damping elements instead of the conventional rigid longitudinal support. This device entails the drawback that only compressive forces between the pedicle screws may be absorbed. The damping elements moreover being of a fixed length, the design of this document provides a substantial number of such damping elements of different lengths in order to allow affixing a damping element of appropriate length between two implanted pedicle screws. Such a design is awkward and entails storing a significant number of damping elements of different lengths.

Another spinal fixation device is known from the European patent document 0,669,109 B which consists of a number of pedicle screws with pierced heads, said screws being connected to each other not by the conventional longitudinal rigid support but by an elastic plastic band that can be pulled through the boreholes in the pedicle screws. Hollow-cylindrical bracing elements that may absorb any compressive forces between pedicle screws are arrayed on the plastic band between the individual pedicle screws. This device incurs many drawbacks. In the first place the plastic band and the bracing elements must be threaded into or between the boreholes of the pedicle screws which already have been implanted, entailing complexity and loss of time for the surgeon. In the second place the somewhat elastic band is not prestressed. Because the supporting body length is fixed in this device too, nominal rupture sites at the support body are proposed to allow the surgeon to cut said body to size during the surgery. This is a complex and time-consuming procedure for the surgeon and might in general result in too short a bracing element, as a result of which its damping would be effective only after a given delay—this circumstance manifestly being undesirable.

The objective of the present invention is palliation of the above drawbacks. The invention aims to create a combined, prestressed tensile-compressive element which is affixable between two pedicle screws or pedicle hooks and which on one hand acts as a tensile spring element of a given spring rate and on the other hand as a compressive element having another spring rate.

BRIEF SUMMARY OF THE INVENTION

In the preferred embodiment of the damping element of the invention, one of the spring elements is mounted as a compression spring. When the damping element has been installed, the connectors configured at the ends of the spring elements touch the ends of the compression spring element, as a result of which the first spring element may be tensively loaded and be prestressed.

Essentially the advantages of the invention are as follows:
the damping properties may be varied by selecting inner cylinders of different lengths,
the prestressing force already present in the pre-assembled state of the damping element is clearly defined and may be made available to the surgeon in selectable form in relation to the different patient body weights and the different indications, and
following traction applied to the vertebrae, the damping elements may be inserted in simple manner between the pedicle screws and be affixed to them.

In a further embodiment mode of the damping element of the present invention the two connectors are detachably affixed to the spring elements. The linkage between the connectors and the minimum of one spring element preferably is implemented by a threaded connection. Moreover different connections matching the particular requirements of different cases may be used. In addition the damping element of the invention constitutes a unitary tensile-compressive element of variably adjustable length.

In another embodiment mode of the damping element of the invention, at least one of the two connectors is integral with at least one of the spring elements. This configuration allows greater compactness of the damping element of the invention.

The connectors may be in the form of bars or bushes depending on the particular application of the damping element of the invention, each connector always being configured coaxially with the longitudinal axis at one end of the spring elements. The bush exhibits preferably a central borehole coaxial with the longitudinal axis and is fitted with locking elements to lock a bar inserted into the central borehole. This design of the damping elements allows connecting coaxially with the longitudinal axis a bar-shaped affixation element or a bar-shaped connector of a further damping element with the bush-shaped connector of the first damping element.

Preferably the locking elements include at least one screw which can be screwed transversely to the longitudinal axis into the bush and which locks a bar-shaped element inserted into bush central bore. By using a stud which radially does not project above the bush as a locking element, the damping element may be made compact, this feature being advantageous when using the damping element in a vertebra stabilizing device.

Depending on the particular damping element application, the connectors at both ends of the spring elements may both be bar-shaped, may both be bushes, or one may a bush and the other may be bar-shaped.

Regarding an application of one or more damping elements of the invention in a device stabilizing adjacent vertebrae, preferably one of the connectors is affixed to a pedicle screw or a pedicle hook and is connected by the second connector to a bar-shaped longitudinal support. The design of the connector elements is such that one of the connectors is a bush and the second connector bar-shaped. The longitudinal support is inserted into the bush central bore and is affixed in this bush by the locking elements, the bar-shaped connector also being affixable in the receiving means conventionally in the form of ducts at the pedicle screws or pedicle hooks. Preferably the bar-shaped connectors are of a length exceeding that of the receiving elements to allow axially displacing and adjusting the damping element as needed.

In order to simplify a combined use of bar-shaped connectors, for instance longitudinal supports and damping elements of the invention, in a device stabilizing adjacent vertebrae, the diameter D of the central borehole of the connector in the form of a bush and the diameter d of the bar-shaped connector are selected so that $D \cong d$.

In another embodiment mode of the damping element of the invention, the spring elements are designed to exhibit a constant spring rate. As a result the state of the unloaded spring element may be restored when the load of the damping element is removed.

In another embodiment mode of the damping element of the invention, its cross-section orthogonal to the longitudinal axis is kidney-shaped. The advantages of this design are that when implanting one or more damping elements, for instance within a spinal affixation, said elements may be situated more favorably as regards vertebral extension or other implant components.

In a further embodiment mode of the damping element of the invention, the second spring element is configured inside the first spring element. The second spring element preferably is a compression spring, whereby at least the first spring element may be prestressed when the damping element has been assembled. Moreover the two spring elements preferably shall be concentric. This embodiment mode also offers the advantage of offering of a damping element of small outside dimensions.

In yet another embodiment mode of the damping element of the invention, the second spring element mounted inside said element and in the form of a compression spring comprises a central borehole which is coaxial with the longitudinal axis, the diameter of said borehole preferably corresponding to the central borehole in the bush. This feature allows longer axial guidance of a bar-shaped component inserted into the central boreholes and provides thereby higher strength of connection between the damping element and the bar-shaped component.

In another embodiment mode of the damping element of the invention, the first spring element is a helical spring. The helical slot of the compression spring preferably is sealed off by a complementary, helical and elastically deforming elevation at the second spring element. The helical spring also may comprise several coils. Preferably the second spring element may be cast into the first spring element already in place.

In one embodiment if the damping element of the invention, the compression spring acting as a spring element is made of a polymer, preferably a polycarbon urethane.

In a further embodiment mode of the damping element of the invention, the bush-shaped connector is integral with the spring element and as a result damping element manufacture is made easier. Furthermore damping element configurations also are feasible wherein both connectors are integral with the first spring element.

In many embodiments of the damper element of the invention the spring constant F of the first spring element and the spring constant f of the second spring element are different. The two spring constants F, f may differ by a factor of at least 1.2, preferably at least 5. This feature offers the advantage that the damping element spring forces in the presence of tensive or compressive load are different. Depending on the field of application of the damping element, the spring constants may differ by a factor between 10 and 100.

In further embodiments modes of the damping element of the invention, the spring rate f of the second damping element is between 50 N/mm and 5,000 N/mm, preferably between 100 N/mm and 2,000 N/mm.

Further advantageous embodiments of the invention are defined in the dependent claims.

Essentially the device of the present invention to stabilize adjacent vertebrae comprises several pedicle screws or pedicle hooks which can be connected by various connectors. Illustrative connectors between two pedicle screws or pedicle hooks are bar-shaped longitudinal supports, springs or damping elements of the invention.

In the preferred embodiment of the device of the present invention, the pedicle screws or pedicle hooks comprise receiving means to receive the affixation element—for instance bar-shaped longitudinal supports—in axially displaceable manner as regards the bar-shaped connectors, at the damping elements of the invention. To lock the affixation elements in the receiving means, the pedicle screws or pedicle hooks are fitted with illustratively end-side locking means which may be in the form of clamping screws or clamping nuts. By using rigid elements such as longitudinal supports on one hand and damping elements on the other hand, the device of the invention may be matched in its mechanical strength to the particular conditions.

Another embodiment mode of the device of the invention, comprises at least one pedicle screw or one pedicle hook which at the same time allows receiving two parallel longitudinal affixation elements. In this manner an element acting as a spring, for instance a damping element of the invention, may be used for affixation of at least one pedicle screw fitted with receiving means or a pedicle hook to a further, adjacent pedicle screw or pedicle hook.

Pedicle screws or pedicle hooks that are fitted with receiving means allowing concurrent connection between two parallel, longitudinal affixation elements and the pedicle screw or pedicle hook are known for instance from U.S. Pat. No. 4,653,481 (Howland). Similarly to the longitudinal supports cited in said patent, the damping elements of the present invention may be affixed by means of bars mounted on the connectors parallel to the longitudinal axis for instance in parallel ducts to the screw heads. Very easily and without further manipulation, the damping element displaceability in the ducts parallel to the longitudinal axis allows inserting a damping element of the present invention—which was prestressed to a desired spring force before implantation—into the receiving means at the pedicle screws. The compensation in length at different spacings between the pedicle screws or pedicle hooks is implemented by the axial displaceability of the bar-shaped connectors which are configured end-wise parallel to the longitudinal axis and which are situated at the damping elements of the invention in the ducts that are also parallel to the longitudinal axis.

Illustratively prestressing the damping element allows taking into account a number of instabilities, indications or patient weight. In the case of extension of the pertinent spinal segments, the damping element is compressed, whereas in the case of flexion of the pertinent spinal segment it is tensioned. The selections of the spring material, for instance a polymer, preferably a polycarbonate urethane (PCU) for the compressively loaded spring, and of metal for the tensively loaded spring element, of the geometric dimensions as well as the prestressing of the tensively loaded spring element allow optimally matching the device of the present invention to a patient's biomechanical particulars.

Essentially the advantages of the device of the present invention are as follows:
- harmonic transition in rigidity from the stabilized spinal segment to the healthy spinal segments,
- the damping elements may be combined selectively in segments with rigid bars.

BRIEF DESCRIPTION OF THE DRAWINGS

The invention and further design modes of it are elucidated below in relation several illustrative modes of implementation shown in partly schematic manner.

DETAILED DESCRIPTION OF THE INVENTION

Figure 1:
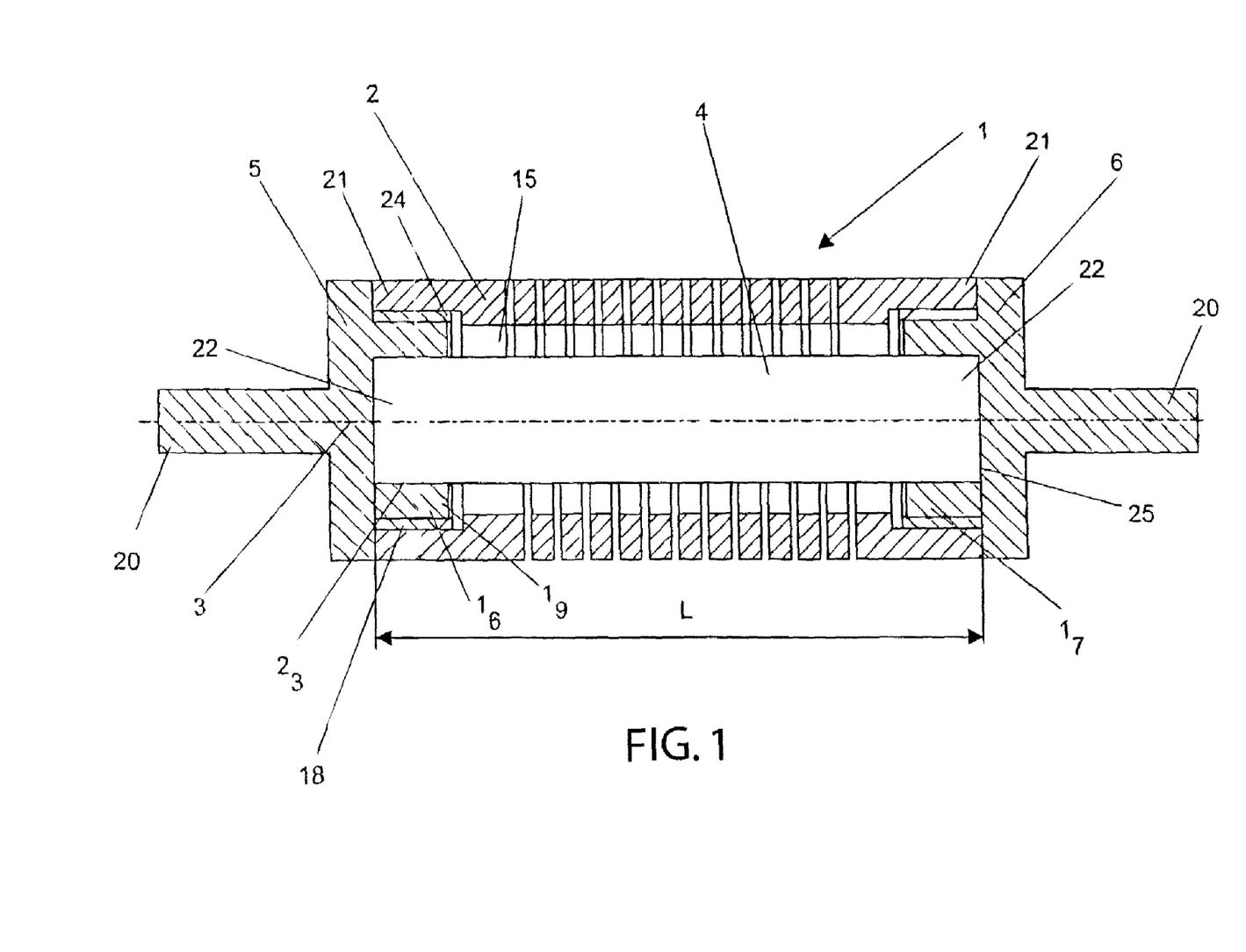
FIG. 1 is a longitudinal section of one embodiment mode of the damping element of the invention.

FIG. 1 shows an embodiment mode of the damping element 1 of the invention having two spring elements 2, 4 concentrically mounted with the longitudinal axis 3. The first spring element 2 is designed as a helical spring with a central cavity 15, whereas the second spring element 4 is bar-shaped and configured in said cavity 15. The end-side connectors 5, 6 also are mounted coaxially with the longitudinal axis 3 and each is fitted with a threaded segment 16, 17 with an outer thread 18, said segments being coaxial with the longitudinal axis 3 and pointing toward the spring elements 2, 4. The first spring element 2 is fitted at its axial ends 21 with inner threads 24 in the cavity 15 which match the outer threads 18, as a result of which the threaded segments of the connectors 5, 6 can be screwed into the first spring element 2. Moreover each connector 5, 6 comprises an open recess 23 configured coaxially with the longitudinal axis 3 at the inner end 19 of said connector, as a result of which the bar-shaped second spring element 4 can be received at its axial ends 22 in said recesses 23. The connectors 5, 6 also are coaxially bar-shaped at their outer end 20. When the damping element 1 is assembled, the ends 22 of the second spring 4 rest against the end faces 25 of the recesses 23 orthogonal to the longitudinal axis 3, and as a result the connectors 5, 6 are a distance L between these end faces 25. This distance L as well as the length of the undeformed first spring element 2 are selected in such a way that when the threaded segments 16, 17 are screwed into the inner threads 24, the first spring element 2 is stretched by a desired length and as a result prestressing is imparted to the damping element 1.

Figure 2:
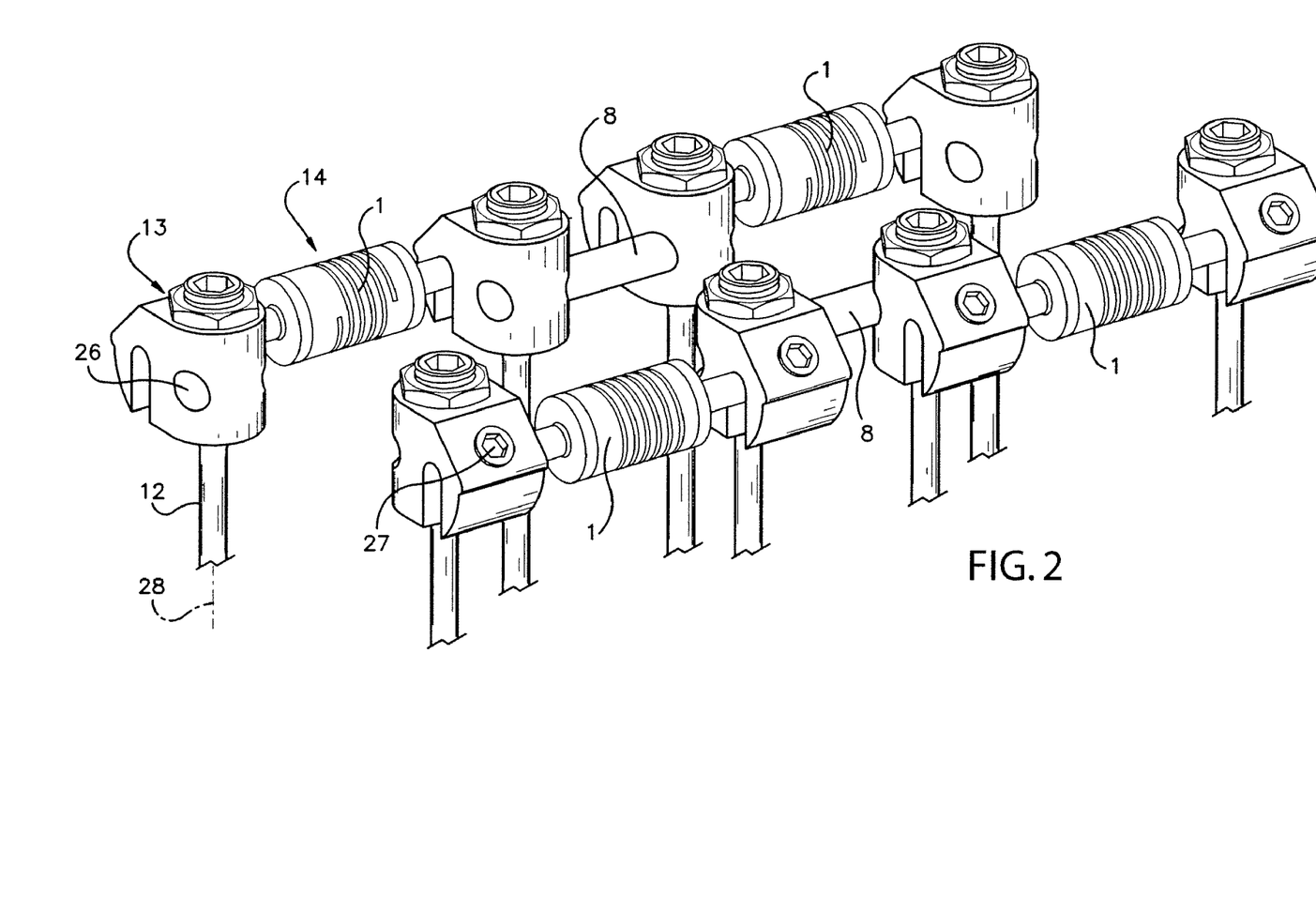
FIG. 2 is a view of an embodiment mode of the device of invention stabilizing adjacent vertebras.

FIG. 2 shows an embodiment mode of the device of the invention illustratively as a device stabilizing adjacent vertebrae (omitted). Several pedicle screws or hooks 12 are affixed to the pedicles of vertebrae to be connected so that their central axes 28 are configured transversely to the spinal column's longitudinal axis. The receiving means 13 at the pedicle screws or hooks 12 are mounted perpendicularly to the central axes 28 and are designed as ducts 26. The bar-shaped outer ends 20 of the connectors 5, 6 (FIG. 1) may be inserted into said ducts 26 and consequently the damping elements 1 are axially displaceable in the ducts 26 before being locked in place by screws 27 relative to the pedicle screws or hooks 12. The receiving means 13 at the pedicle screws or hooks 12 each comprise two parallel ducts 26 and allow locking for instance a bar-shaped affixation means 7 at a pedicle screw or hook 12 next to a damping element 1.

Figure 3:
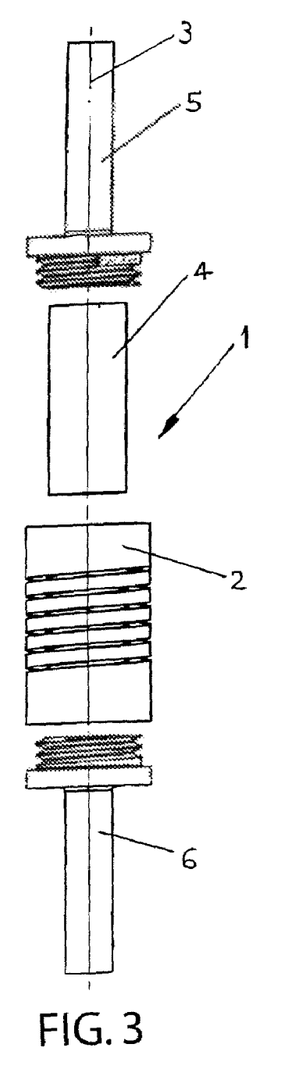
FIG. 3 is an exploded view of an embodiment mode of the damping element of the invention.

FIG. 3 shows an embodiment mode of the damping element 1 of the invention which comprises a first spring element 2 in the form of a helical spring, a bar-shaped second spring element 4 and two connectors 5, 6 configured coaxially with the longitudinal axis 3.

Figures 4, 5:
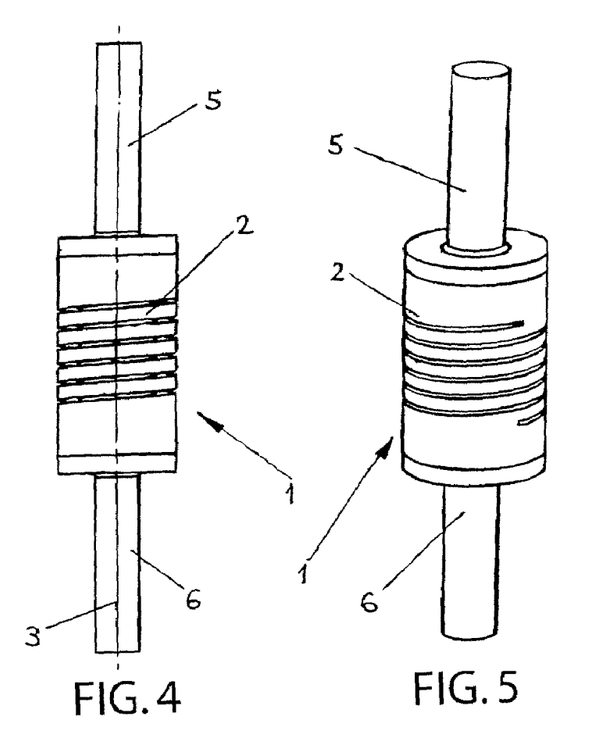
FIG. 4 is an elevation of an embodiment mode of the damping element of the invention.
FIG. 5 is a perspective of an embodiment mode of the damping element of the invention.

FIGS. 4 and 5 shown an embodiment mode of the damping element 1 of the invention comprising a first spring element 2 in the form of a helical spring and two connectors 5, 6 which are connected to the first spring element 2 and which are coaxial with the longitudinal axis 3.

Figure 6:
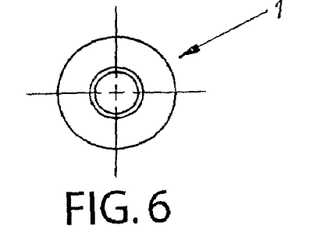
FIG. 6 is a top view of an embodiment mode of the damping element of the invention.

FIG. 6 is an embodiment mode of the damping element 1 of the invention which exhibits a circular cross-section orthogonally to the longitudinal axis 3. Other cross-sectional shapes, for instance oval or elliptical cross-sections, that might be advantageous in implanting the damping element 1 also are conceivable.

Figure 7:
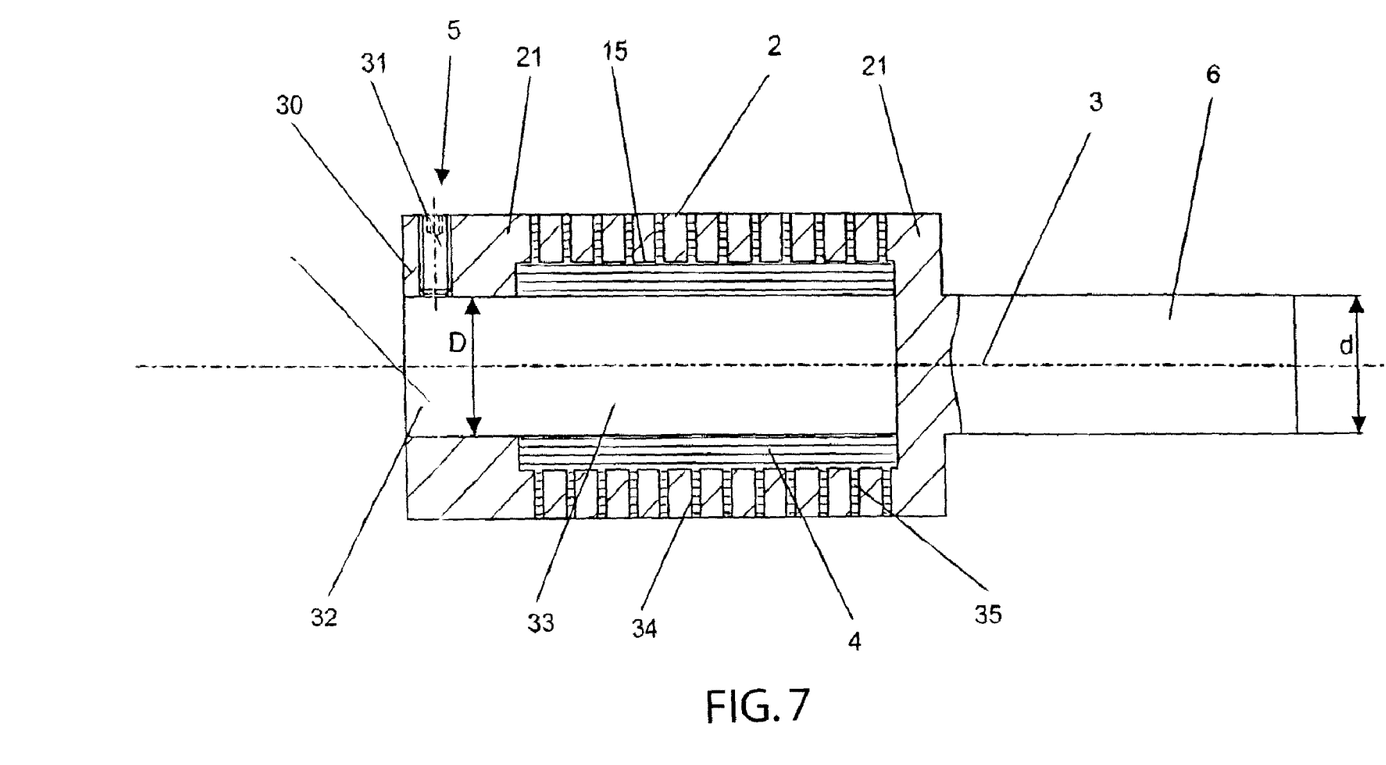
FIG. 7 is a longitudinal section of an embodiment mode of the damping element of the invention.

FIG. 7 shows an embodiment mode of the damping element 1 of the invention which comprises a circular-cylindrical helical spring acting as a first spring element 2 mounted coaxially with the longitudinal axis 3. This first spring element 2 is fitted with a helical slot 34 and with a cavity 15 that is open only at one end 21 of the first spring element 2 and is coaxial with the longitudinal axis 3. A connector 5, 6 is situated at each of the axial ends 21, the two connectors 5, 6 of this embodiment mode being integral with the spring element 2. The first connector 5 is in the form of a bush 30 comprising a central borehole 32 that is coaxial with the longitudinal axis 3, whereas the second connector 6 is designed as a bar also coaxial with the longitudinal axis 3. The second bar-shaped connector 6 is mounted at the end 21 of the first spring element 2 where the cavity 15 is axially closed. The diameter of the central borehole 32 in the first connector 5 is D. The second connector 6 also is circular-cylindrical and comprises a diameter d which in the shown embodiment mode of the damping element 1 is the same size as the diameter D of the central borehole 32 in the first connector 5. Illustratively a longitudinal bar belonging to the vertebral stabilizing device or the second bar-shaped connector 6 of a further damping element 1 may be inserted into the central bore hole 32. Using locking means 31, which in the shown embodiment mode of the damping element 1 are designed as studs screwed transversely to the longitudinal axis 3 into the bush 30, said bar being insertable into and locked in the central borehole 32. The second spring element 4 is configured coaxially with the longitudinal axis 3 in the cavity 15 of the first spring element 2 and comprises an elastically deforming, helical elevation 35 which is complementary to the helical slot 34 in the first spring element 2, said elevation 35 sealing off the slot 34 in the first spring element 2. Moreover the second spring element 4 is fitted with a central borehole 33 coaxial with the longitudinal axis 3 and being of the same diameter as the central borehole 32 in the bush 30.

Figure 8:
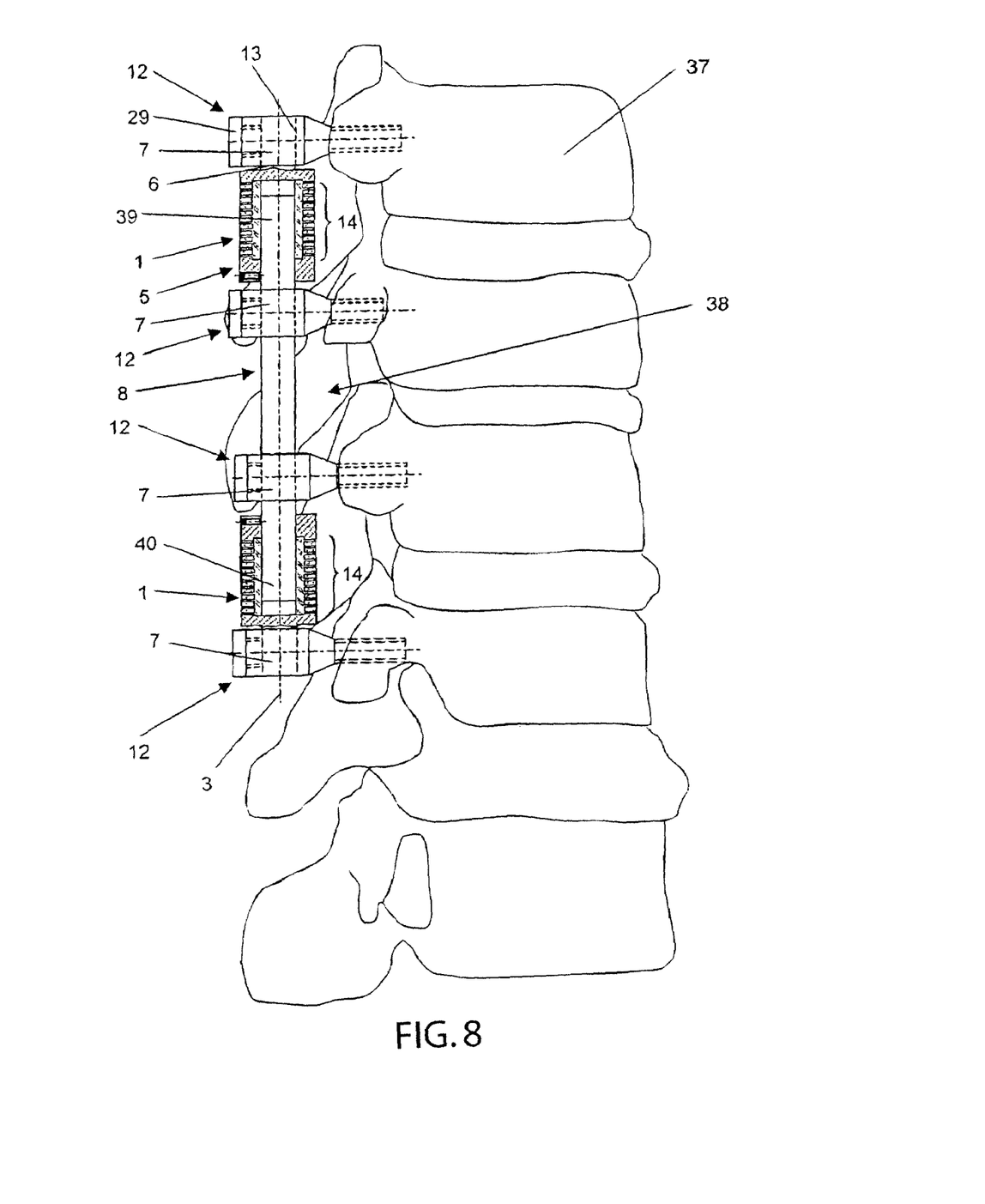
FIG. 8 is an elevation of an embodiment mode of the device of the invention when used to stabilize adjacent vertebrae.

FIG. 8 shows one embodiment mode of the device 38 of the invention when used to stabilize adjacent vertebrae 37. One pedicle screw 12 is screwed into each of four adjacent vertebrae 37. The device 38 coaxial with the longitudinal axis 3 comprises each time a spring acting as the element 14 between one of the outer four adjacent vertebrae 37 and one of the adjacent inner vertebrae 37 as well as a bar-shaped longitudinal support 8 between the two adjacent inner vertebrae 37. The elements 14 acting as springs are composed of damping elements 1 comprising at each of one of their ends 21 (FIG. 7) a bar-shaped connector 6 and at the other end 21 a bush 30 (FIG. 7). The bar-shaped connectors 6 act as affixation means 7 which are inserted into the receiving means 13 of the two pedicle screws 12 which are situated end-side relative to the device 38 and which at that location are detachably connected by the screws acting as locking means 29 to the pedicle screws. The connectors 5 of the damping elements 1 are designed as bushes 30 (FIG. 7) and point toward the inner two of the four vertebrae 37 which must be stabilized. A bar-shaped longitudinal support 8 is inserted between the two damping elements 1, the longitudinal support 8 being designed in a manner that the affixation elements 7 in the receiving means 13 of the two inner pedicle screws 12 are constituted by axial segments of the longitudinal support 8. The longitudinal support 8 is connected on one hand by means of the screws acting as locking means 29 of the two inner pedicle screws 12 to the device 38 and on the other hand is inserted at its two ends 39, 40 into the central boreholes 32, 33 into the connectors 5 and the second spring elements 4 (FIG. 7) and detachably locked there by the locking means 31 (FIG. 7). Other combinations of longitudinal support 8 and damping elements 1 coaxial with the longitudinal axis 3 also are feasible depending on particular applications. Several longitudinal supports 8 may be used for instance instead of one, or the longitudinal support(s) 8 also may be replaced by connectors 6 at one or several damping elements 1 which in this instance then must exhibit sufficient length. Moreover the longitudinal axis 3 may be curved or angled in various applications of the device 38 of the invention.

Figure 9:
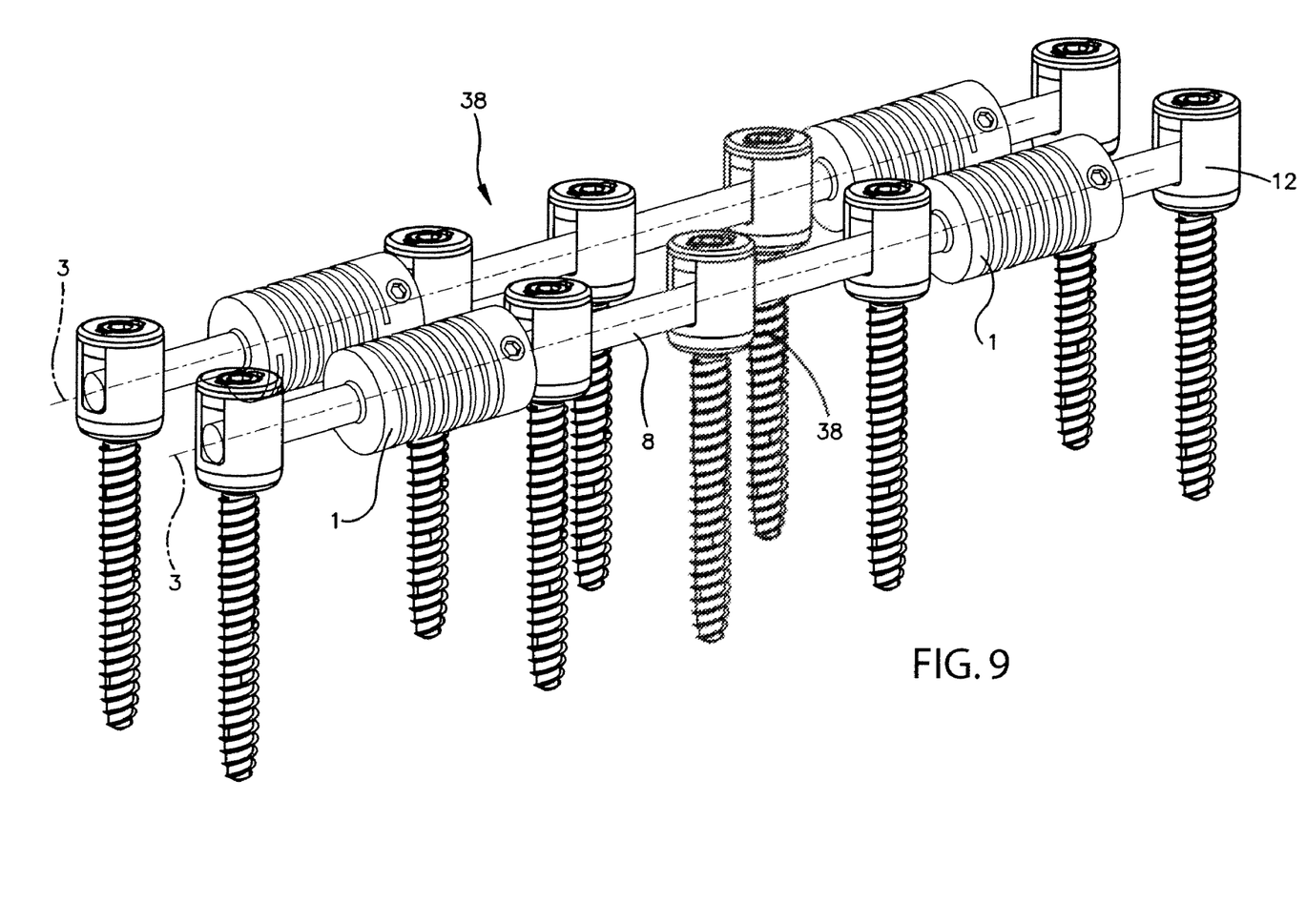
FIG. 9 is a perspective of an embodiment mode of the device of the invention.

FIG. 9 shows an illustrative embodiment mode of the device of the invention which differs from the embodiment mode shown in FIG. 8 only in that it comprises two devices 38 parallel to the longitudinal axes 3, each time with two axially end-side damping elements 1 and one longitudinal support 8 configured in-between. Furthermore five pedicle screws 12 are provided each time.

The invention claimed is:

1. A damping system comprising:
a damping element including two spring elements coaxial with or parallel to a longitudinal axis of the damping element, and two axially mounted end connectors wherein:
the first spring element comprises a helical spring having a helical slot and a central cavity,
the second spring element is disposed within the cavity of the first spring element and comprises an elastically deforming, helical elevation which is received within the first spring element and a central borehole coaxial with the longitudinal axis of the damping element,
the first end connector having a central borehole which is coaxial with the longitudinal axis of the damping element,
the second end connector being linked to the first spring element; and
at least two bone fixation elements selected from the group consisting of pedicle screws and pedicle hooks, wherein each of the bone fixation elements includes a duct for receiving the end-side connectors so that the damping element can span adjacent vertebra.

2. The damping system of claim 1, wherein the connectors are integral with at least one of the spring elements.

3. The damping system of claim 1, wherein the second end connector has a diameter d and is mounted at the end of the first spring element where the cavity is axially closed.

4. The damping system of claim 3, wherein the diameter of the central borehole of the first connector is D which is substantially equal to d.

5. The damping system of claim 1, wherein the diameter of the central borehole of the second spring element is substantially equal to the diameter of the central borehole of the first connector.

6. The damping system of claim 1, wherein the first spring element includes an open end and a closed end, the second end connector being linked to the first spring element at the closed end.

7. The system stabilizing adjacent vertebrae of claim 6, wherein at least one longitudinal support is located between two inner adjacent vertebrae.

8. The system stabilizing adjacent vertebrae of claim 6, wherein the second end connector acts as an affixation means by inserting into the duct of at least one bone fixation element.

9. The damping system of claim 1, wherein the central cavity of the first spring element and the central borehole of the first connector is sized and configured to receive one of a spinal rod or an end connector of an adjacent damping system.

10. A system stabilizing adjacent vertebrae, comprising:
at least one damping system comprising:
two spring elements coaxial with or parallel to a longitudinal axis of the damping element, and two axially mounted end connectors wherein:
the first spring element comprises a helical spring having a helical slot and a central cavity,
the second spring element is disposed within the cavity of the first spring element and comprises an elastically deforming, helical elevation which is received within the first spring element and a central borehole coaxial with the longitudinal axis of the damping element,
the first end connector having a central borehole which is coaxial with the longitudinal axis of the damping element,
the second end connector being linked to the first spring element;
at least one longitudinal support; and
N bone fixation elements selected from the group consisting of pedicle screws and pedicle hooks, where $N \leq 3$, wherein each of the bone fixation elements includes a duct for receiving the end connectors or the longitudinal support.

11. The system stabilizing adjacent vertebrae of claim 10, wherein at least one damping system is located between one of the outer adjacent vertebrae and one of the inner adjacent vertebrae.

12. The system stabilizing adjacent vertebrae of claim 11, wherein the bone fixation element is detachably connected to the second connector by a locking mechanism.

13. The system stabilizing adjacent vertebrae of claim 10, wherein one axial end of the longitudinal support is connected to the bone fixation element by a locking mechanism and the other axial end of the longitudinal support is inserted into the central borehole of the first connector and the second spring element.

14. A system stabilizing adjacent vertebrae, comprising: two devices, each device comprising:
   at least one damping system comprising: two spring elements coaxial with or parallel to a longitudinal axis of the damping system, and two axially mounted end connectors wherein:
      the first spring element comprises a helical spring having a helical slot and a central cavity,
      the second spring element is disposed within the cavity of the first spring element and comprises an elastically deforming, helical elevation which is received within the first spring element and a central borehole coaxial with the longitudinal axis of the damping system,
      the first end connector having a central borehole which is coaxial with the longitudinal axis of the damping system,
      the second end connector being linked to the first spring element;
   at least one longitudinal support; and
   N bone fixation elements selected from the group consisting of pedicle screws and pedicle hooks, where $N \leq 5$, wherein each of the bone fixation elements includes a duct for receiving the end connectors or the longitudinal support.

* * * * *